United States Patent [19]

Sandoval et al.

[11] Patent Number: 5,220,077
[45] Date of Patent: Jun. 15, 1993

[54] ALKOXYLATION PROCESS

[75] Inventors: Tonyette S. Sandoval; Peter A. Schwab, both of Travis County, Tex.

[73] Assignee: Vista Chemical Company, Houston, Tex.

[21] Appl. No.: 932,294

[22] Filed: Aug. 19, 1992

[51] Int. Cl.$^5$ .............................................. C07C 41/03
[52] U.S. Cl. ..................................... 568/618; 502/171
[58] Field of Search ......................................... 568/618

[56] References Cited

U.S. PATENT DOCUMENTS 4,775,653 10/1988 Leach et al. ......................... 568/618

Primary Examiner—Howard T. Mars
Attorney, Agent, or Firm—Browning, Bushman, Anderson & Brookhart

[57] ABSTRACT

A process for preparing an alkoxylation catalyst in which a catalyst is formed by admixing an alkoxylated alcohol with a calcium or strontium containing compound which is dispersible in the alkoxylated alcohol, an inorganic acid and a titanium alkoxide, the pre-mix optionally being heated to a temperature and for a time sufficient to effect at least partial exchange reaction between the alkoxide groups of the titanium alkoxide and the hydroxyl groups of the alkoxylated alcohol, the pre-mix being used in an alkoxylation process to alkoxylate active hydrogen containing compounds such as alcohols.

13 Claims, No Drawings

ALKOXYLATION PROCESS

BACKGROUND OF THE INVENTION

1. Field of the Invention

The present invention relates to a process for the preparation of alkylene oxide adducts of active hydrogen compounds such as alcohols and to a process for preparing catalysts useful in such alkoxylation reactions.

2. Description of the Prior Art

Alkylene oxide adducts of hydrogen compounds find utility in a variety of products such as, for example, surfactants, solvents, chemical intermediates, etc. Typically, these alkylene oxide adducts are prepared by an addition or alkoxylation reaction in which an alkylene oxide, such as ethylene oxide, is reacted under suitable conditions with an organic compound, such as an alcohol, having one or more active hydrogen atoms. In particular, ethylene oxide adducts of aliphatic alcohols or substituted phenols having from about 8 to 20 carbon atoms have found widespread utility as non-ionic detergent components of cleaning formulations for use in industry and in the home.

The alkoxylation reaction produces a product mixture of various alkoxylate molecules having a variety of alkylene adducts (oxyethylene adducts). Because the number of oxyalkylene adducts or oxyalkylene groups effect the properties of the product, it is desirable to tailor the adduct number distribution of a given product mixture to its intended service. For example, it is known that in surfactant applications, an adduct with too few ethylene oxide molecules is not effective because of poor water solubility, while an adduct with too many ethylene oxide molecules is undesirable because surface tension reduction per unit mass decreases drastically with increasing molecular weight. Thus, as taught in U.S. Pat. No. 4,239,917, it is desirable, particularly for surfactant applications, to use ethoxylates or alkoxylates with a narrow or peaked distribution in the desired mole adduct range of from about 5 to about 10 alkylene oxide adducts per alkylate molecule.

PCT Application WO85/00365 discloses an alkoxylation process which utilizes a calcium based catalyst to produce alkoxylation products having a narrow or peaked distribution of alkoxylation species.

U.S. Pat. No. 4,775,653 discloses a process for making another type of calcium based alkoxylation catalyst which utilizes aluminum alkoxides, the catalysts being useful in the preparation of alkoxylation products having a narrow or peaked distribution of the alkoxylation species.

SUMMARY OF THE INVENTION

It is therefore an object of the present invention to provide a novel process for preparing alkoxylation catalysts.

It is further an object of the present invention to produce a catalyst for alkoxylation reactions which is less sensitive to air than prior art calcium based catalysts using aluminum alkoxides.

Another object of the present invention is to provide a process for preparing alkoxylation product mixtures having a narrow alkoxylation product distribution.

The above and other objects of the present invention will become apparent from the description given herein and the appended claims.

In one aspect, the present invention provides a process for preparing an alkoxylation catalyst in which a catalyst pre-mix is formed by admixing an alkoxylated alcohol, as alkaline earth metal containing compound containing calcium or strontium which is at least partially dispersible in the alkoxylated alcohol, an inorganic acid and a titanium alkoxide, the alkaline earth compound being added prior to the addition of the titanium alkoxide. The catalyst pre-mix is then, optionally, heated to a temperature and for a time sufficient to effect at least a partial exchange reaction between the alkoxide groups of the titanium alkoxide and the hydroxyl group of the alkoxylated alcohol to thereby form an active alkoxylation catalyst. In a variation, the catalyst can be formed in situ during the alkoxylation process.

In another aspect, the present invention provides a process for the alkoxylation of an alcohol in which the alkoxylation catalyst prepared by the method described above is used in a process wherein an alcohol reactant and an alkylene oxide are brought together, in the presence of the alkoxylation catalyst and under typical alkoxylation conditions, to thereby produce alkoxylated derivatives of the alcohol reactant.

DETAILED DESCRIPTION OF THE PREFERRED EMBODIMENT

In preparing the alkoxylation catalyst according to the process of the present invention, a catalyst pre-mix can be first formed by admixing an alkoxylated alcohol, an alkaline earth containing compound which is at least partially dispersible in the alkoxylated alcohol, an inorganic acid and a titanium alkoxide. The alkoxylated alcohols, i.e., the dispersants, useful in forming the catalyst are those having the general formula $R_1-O(C_mH_{2m}-O)_nH$ wherein $R_1$ is a hydrocarbon radical containing from 1 to about 30 carbon atoms, n is an average and is from about 2 to about 20 and m is from 2 to 4. Particularly useful are alkoxylated alcohols wherein $R_1$ is from about 6 to about 14, most preferably from about 8 to about 12. In the preferred alkoxylated alcohols, n is from about 1 to about 12, most preferably from about 1 to about 4 and m is 2. Thus, ethoxylates of fatty alcohols such as octanol, decanol and dodecanol wherein there are from about 1 to about 12 and most preferably from 1 to 4 moles of ethylene oxide are especially preferred. The $R_1$ group is generally an organic residue of an aliphatic alcohol which may be of branched or straight chain structure, although preferably, particularly for surfactant use, it is preferred that greater than 50%, more preferably greater than 60% and most preferably greater than 70% of such alcohol molecules are of linear (straight chain) carbon structure.

Specific examples of primary, straight chain monohydric aliphatic alcohols from which the $R_1$ group can be derived include ethanol, hexanol, octanol, decanol, dedecanol, tetradecanol, pentadecanol, octadecanol, eicosanol, etc. Examples of branched chain or secondary alcohols from which the $R_1$ group can be derived include isopropanol, isoheptanol, 3-heptanol, isodecanol, 2-methyl-1-nonanol, 2-methyl-1-undecanol, 4-tetradecanol, 4-hexadecanol, etc.

The alkoxylated alcohols used in the catalyst forming process of the present invention can be prepared by methods well known in the art for preparing ethylene oxide adducts of alcohols. Alternately, the ethylene oxide adducts can be prepared according to the process of the present invention or according to the process of U.S. Pat. No. 4,775,653, incorporated herein by reference for all purposes.

The alkaline earth metal containing compound used in the process of the present invention is one which is at least partially dispersible in the alkoxylated alcohol. As used herein, the term "dispersible" refers to such a compound which solubilizes or otherwise interacts with the alkoxylated alcohol in such a manner that it becomes a new species of alkaline earth metal compound. It is to be understood however that, inasmuch as the mechanism is not completely understood, the term "dispersible" or "soluble" is not intended to be limited to the formation of a truly dissolved alkaline earth metal species as would be commonly understood in the case of ordinary solubilization. The alkaline earth metal is either calcium or strontium, calcium being preferred. While compounds such as calcium and/or strontium hydride, calcium and/or strontium acetate, calcium and/or strontium oxalate, calcium and/or strontium nitrate, etc. may be used, it is preferred that the alkaline earth metal containing compound be calcium and/or strontium oxide, calcium and/or strontium hydroxide or a mixture thereof.

The inorganic acids useful in the process of the present invention include the acids themselves as well as "acid salts". Thus, non-limiting examples of inorganic acids include sulfuric acid, hydrochloric acid, hydrofluoric acid, phosphoric acid, pyrophosphoric acid, ammonium biflouride, ammonium sulfate, etc. Particularly preferred are the oxy acids, such as sulfuric acid.

The titanium alkoxide used in the process of the present invention will have the general formula

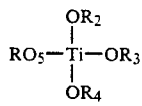

wherein $R_2$, $R_3$, $R_4$, and $R_5$ is each a hydrocarbon radical containing from about 1 to about 30 carbon atoms. Generally speaking, the description set out above with respect to the $R_1$, radical is generally applicable to the $R_2$, $R_3$, $R_4$, and $R_5$ radicals, i.e., those radicals are generally an organic residue derived from an alcohol. The titanium alkoxide (tetralkoxide) can be obtained by reacting a titanium alkyl (tetralkyl) with ethylene followed by oxidation which produces titanium alkoxide in which the chain length of the groups $R_2$, $R_3$, $R_4$, and $R_5$ vary. It will be appreciated that while the groups $R_2$, $R_3$, $R_4$, and $R_5$ can be, and generally are, different from one another, they may all be the same. It is generally preferred to use titanium alkoxides wherein each of the $R_2$, $R_3$, $R_4$, and $R_5$ groups is such as to provide an average chain length of from about 2 to about 14, preferably about 2 to about 8, carbon atoms for each of the $R_2$, $R_3$, $R_4$, and $R_5$ groups. An especially desirable titanium alkoxide is titanium tetraisopropoxide, a commercially available material.

In preparing the catalyst pre-mix, relative amounts of the various components can vary widely. For example, the mole ratio of the alkaline earth compound to the titanium alkoxide can vary from about 1:1 to about 10:1, based on alkaline earth metal and titanium, respectively. The mole ratio of the inorganic acid to the titanium alkoxide can vary from about 0.25:1 to about 4:1, based on the ratio of the acid equivalent e.g. acid hydrogens, in the inorganic acid to the titanium, respectively. It is generally preferred that the combined concentration of the alkaline earth compound, the inorganic acid and the titanium alkoxide be present in the catalyst pre-mix in an amount of from about 1 to about 10% by weight, the alkoxylated alcohol and diluents such as free alcohol being present in an amount of from about 90-99% by weight. Depending on the source and type of the alkoxylated alcohol dispersant, the free alcohol content can range from about 1% by weight to about 60% by weight.

Generally speaking, the order of addition of the various components of the catalyst pre-mix is immaterial with the exception that the alkaline earth compound must be added prior to addition of the titanium alkoxide.

In addition to the above components of the catalyst pre-mix, the pre-mix can contain, with advantage, organic acids such as disclosed in U.S. Pat. No. 4,775,653.

In preparing the catalyst according to the process of the present invention, a typical alkoxylated alcohol dispersant is admixed with a suitable alkaline earth containing compound such as calcium or strontium oxide and the mixture stirred for a suitable period of time until at least some of the alkaline earth compound disperses or solubilizes in the alkoxylated alcohol dispersant. Generally, this is accomplished by stirring, or other means of agitation to achieve intimate and thorough contact, at a temperature of generally from about 25° C. to about 150° C. (usually below the boiling point of the alkoxylated alcohol) for a sufficient period of time. The dispersion time can vary from about 0.5 hours to about 20 hours. Longer times can be used if desired. Once the dispersion has been formed as evidenced, e.g., by the presence of alkalinity, the inorganic acid is then added. In one variation of the process, the titanium alkoxide is then added and stirring of the mixture continued and the mixture heated to a temperature and for a sufficient period of time to effect at least a partial exchange reaction between the alkoxide groups of the titanium alkoxide and the hydroxyl group of the alkoxylated alcohol.

The precise temperature to which the catalyst pre-mix is heated will, of course, depend upon the nature of the components employed to form the pre-mix. However, as noted above, the heating of the catalyst pre-mix to activate it is usually carried out at a temperature and for a period of time sufficient to effect at least a partial exchange reaction between the alkoxide groups of the titanium alkoxide and the hydroxyl group of the alkoxylated alcohol. This point can generally be determined by the evolution of alcohol which distills out of the mixture. While catalyst activation occurs to some extent with any heating in the desired range, activation is best evidenced by the evolution of alcohol as a result of the exchange reaction. However, in order to achieve a highly active catalyst, it is preferred that the heating be carried on until the mixture has reached a substantially constant boiling point. The desired activation temperature should, for a given pressure, approximate the boiling point of a substantial fraction of the free alcohols derived from the $R_2$, $R_3$, $R_4$, and $R_5$ groups of the titanium alkoxide. At this point, maximum exchange has likely occurred between the alkoxide groups of the titanium alkoxide and the hydroxyl group of the alkoxylated alcohol. It will be recognized that when the titanium alkoxide utilized is one where $R_2$, $R_3$, $R_4$, and $R_5$ are long chain, e.g. 8 to 14 carbon atoms and longer, the alcohols produced in the exchange reaction are high boiling. Accordingly, very little if any distillation of alcohol occurs without the application of extremely high temperatures which can cause unwanted side reactions. In such cases, the heating can be carried out to a temperature of about 160°–300° C. and more preferably from about 200°–260° C. Lower temperatures may be employed when the process is conducted under reduced pressure, e.g. at a pressure of about 150–300 Torr, temperatures in the range of about 140° C. to about 210° C. are suitable. Indeed, it has been found that reduced pressure results in highly potent catalyst. For a given catalyst pre-mix, the desired temperature range can be determined by sampling the catalyst dispersion as it is being heated at various times during the heating cycle and subjecting the samples to an ethoxylation reaction. When the desired degree of activity is achieved in the ethoxylation reaction, heating can be discontinued and all future catalyst pre-mix of the same composition heated to that temperature, and, of course, for that period of time. Generally, however, the time of heating can vary from about 0.1 hour to about 5 hours, generally in the range of from about 0.2 hour to about 1 hour.

It has been found that, if after the catalyst is prepared it is aged, e.g., by allowing it to stand at room temperature, activity can be greatly enhanced. Although the aging time for a given catalyst pre-mix will, of course, depend upon the components of that pre-mix, the desired aging time can be determined in a manner similar to that described above with respect to determining the desired temperature and time of heating. Thus, samples of the catalyst which are being aged can be used in ethoxylation reactions and the degree of activity determined. Generally, aging times ranging from about two hours to about one week or longer can be used.

It has been found that, unlike the preferred process disclosed in U.S. Pat. No. 4,775,653, in order to make highly active catalysts, it is not necessary when the catalyst pre-mix is being formed, that any water which is present be removed prior to the addition of the titanium alkoxide. Thus, the catalyst of the present invention is easier to prepare.

To more fully demonstrate the present invention, the following non-limiting examples are presented.

EXAMPLE 1

This example sets forth one general procedure for making the alkoxylation catalyst of the present invention. Into a 500 ml glass beaker was charged 250 g of ALFONIC 1012-40 alkoxylated alcohol dispersant (mixture of 55% by weight $C_{10}$ alcohol and 45% by weight $C_{12}$ alcohol with 40% ethylene oxide adduct marketed by Vista Chemical Company), 22 g $Ca(OH)_2$ and 4 g $H_2SO_4$. The mixture was stirred for at least 4 hours at room temperature after which it was transferred into a stainless steel reactor and subjected to a mild $N_2$ purge. The reactor was heated to 150° C. for 30 minutes to drive off any water. After cooling the contents of the reactor to 90° C., 22 g of titanium tetraisopropoxide was added. The reactor was enclosed, purged with $N_2$ and heated to 190° C. Heating was continued until substantially all of the isopropanol alcohol and free alcohol present in the dispersant had been removed. The reactor was then closed off and a 10 psig $N_2$ blanket maintained on the reactants which were stirred at 190° C. for approximately 10 minutes. The mixture was then cooled down and removed from the reactor.

EXAMPLE 2

Using various amounts of the catalyst prepared according to example 1, a $C_{10}$ alcohol marketed as ALFOL 10 by Vista Chemical Company was ethoxylated. The ethoxylation reaction was conducted at 171°–175° C. and 50 psig ethylene oxide (EO) pressure. Table 1 below gives reaction parameters.

TABLE 1

| RUN NO. | ALCOHOL g | CATALYST g | EO g | REACTION TIME min. |
|---|---|---|---|---|
| 1 | 156 | 1 | 44 | 75 |
| 2 | 108 | 2 | 92 | 50 |
| 3 | 80 | 3 | 120 | 50 |

EXAMPLE 3

The procedure of Example 1 was followed with the exception that only 13 g of $Ca(OH)_2$ was used in preparing the catalyst.

EXAMPLE 4

The procedure of Example 2 was followed with the exception that the catalyst prepared accoring to Example 3 was employed. The reaction parameters are given in Table 2 below.

TABLE 2

| RUN NO. | ALCOHOL g | CATALYST g | EO g | REACTION TIME min |
|---|---|---|---|---|
| 4 | 156 | 2 | 44 | 25 |
| 5 | 108 | 2 | 92 | 45 |

With regard to the ethoxylated alcohols made according to Examples 2 and 4, Table 3 below shows the percent-by-weight ethylene oxide (EO) incorporated into the ethoxylated alcohols and the distribution of the ethoxylation species (adducts). For comparison purposes, ethoxylated alcohols made under corresponding conditions with the catalyst disclosed in U.S. Pat. No. 4,775,653 are also given. In Table 3, the runs made using the catalyst of U.S. Pat. No. 4,775,653 are identified as '653 Catalyst. In all cases, the determination of ethylene oxide adduct distribution was made by liquid chromatography and gas chromatography analysis. In Table 3 and all other similar tables "0" moles of EO is a measure of free alcohol, i.e. un-reacted alcohol.

TABLE 3

| RUN # | | 1 | 4 | '653 CATALYST | 2 | 5 | '653 CATALYST | 3 | '653 CATALYST |
|---|---|---|---|---|---|---|---|---|---|
| % EO | | 21.6 | 21.0 | 21.7 | 46.4 | 46.7 | 46.5 | 59.0 | 60.4 |
| MOLES EO | 0 | 38.9 | 39.4 | 38.2 | 7.2 | 7.1 | 7.0 | 1.4 | 1.2 |
| | 1 | 22.5 | 23.7 | 22.0 | 6.7 | 6.4 | 6.5 | 1.2 | 0.8 |
| | 2 | 17.5 | 16.4 | 18.9 | 11.0 | 10.5 | 11.0 | 2.8 | 2.1 |
| | 3 | 12.7 | 13.1 | 13.6 | 18.9 | 18.9 | 19.4 | 6.5 | 5.1 |
| | 4 | 5.3 | 5.4 | 5.3 | 22.8 | 23.1 | 23.4 | 13.6 | 11.7 |
| | 5 | 2.0 | 1.9 | 1.4 | 18.1 | 18.6 | 17.8 | 20.5 | 18.3 |
| | 6 | | | | 9.5 | 9.8 | 9.6 | 21.4 | 21.1 |
| | 7 | | | | 3.7 | 3.9 | 3.7 | 16.4 | 18.2 |
| | 8 | | | | 1.2 | 1.4 | 1.1 | 9.4 | 11.9 |
| | 9 | | | | | | | 4.2 | 6.0 |

TABLE 3-continued

| RUN # | 1 | 4 | '653 CATALYST | 2 | 5 | '653 CATALYST | 3 | '653 CATALYST |
|---|---|---|---|---|---|---|---|---|
|  |  | 10 |  |  |  |  | 1.5 | 2.4 |

As can be seen from the data in Table 3, using the titanium based catalyst of the present invention, one can obtain an EO distribution which is substantially as narrow or peaked as that obtained using the process and catalyst of U.S. Pat. No. 4,775,653.

EXAMPLE 5

The general procedure of Example 1 was used to prepare a series of catalysts employing a strontium based compound rather than a calcium based compound. Catalyst pre-mixes were made using the formulations given below:

| Catalyst A | 250 g | NOVEL II 8-40[1] ethoxylated alcohol |
|---|---|---|
|  | 79 g | $Sr(OH)_2 \cdot 8H_2O$ |
|  | 4 g | $H_2SO_4$ |
|  | 11 g | Titanium IV isopropoxide |
| Catalyst B | 125 g | NOVEL II 8-40 ethoxylated alcohol |
|  | 38.5 g | $Sr(OH)_2 \cdot 8H_2O$ |
|  | 11 g | Titanium IV isopropoxide |
| Catalyst C | 125 g | NOVEL II 8-40 ethoxylated alcohol |
|  | 38.5 g | $Sr(OH)_2 \cdot 8H_2O$ |
|  | 4 g | $H_2SO_4$ |
|  | 11 g | Titanium IV isopropoxide |

[1]$C_8$ alcohol ethoxylated with 40% by weight ethylene oxide (Experimental Material).

EXAMPLE 6

Using the catalyst prepared according to Example 5, ALFOL 10 alcohol was ethoxylated as per the procedure of Example 2. Reaction parameters are shown in Table 4 below.

TABLE 3

|  | ALCOHOL g | CATALYST g | EO g | REACTION TIME min |
|---|---|---|---|---|
| CATALYST A | 81 | 1 | 69 | 64 |
| CATALYST B | 81 | 1 | 69 | 54 |
| CATALYST C | 81 | 1 | 69 | 129 |

The weight percent ethylene oxide of the ethoxylated alcohols and the distribution of the ethylene oxide adducts is shown in Table 5 below. For comparative purposes, corresponding data for an ethoxylated alcohol prepared using a catalyst such as disclosed in U.S. Pat. No. 4,775,653 is also included.

TABLE 5

|  |  | '653 Catalyst | Catalyst A | Catalyst B | Catalyst C |
|---|---|---|---|---|---|
| % EO |  | 46 | 46 | 46 | 43 |
| Moles | 0 | 7.0 | 9.1 | 9.5 | 11.4 |
| EO | 1 | 6.5 | 8.2 | 8.4 | 9.6 |
|  | 2 | 11.0 | 11.6 | 11.5 | 13.7 |
|  | 3 | 19.4 | 16.6 | 16.4 | 17.2 |
|  | 4 | 23.4 | 17.6 | 17.7 | 16.9 |
|  | 5 | 17.8 | 15.0 | 15.0 | 13.5 |
|  | 6 | 9.6 | 10.4 | 10.4 | 8.9 |
|  | 7 | 3.7 | 6.1 | 6.0 | 4.9 |
|  | 8 | 1.1 | 3.1 | 3.1 | 2.4 |
|  | 9 |  | 1.4 | 1.4 | 1.1 |

EXAMPLE 7

The procedure of Example 1 was employed to prepare a catalyst with the exception that rather than using ALFONIC 1012-40 ethoxylated alcohol as a dispersant, the dispersant was a mixed $C_{12}$–$C_{15}$ alcohol (55% branched chain) ethoxylated with 30% by weight ethylene oxide.

The thus prepared catalyst was used as per the procedure of Example 2, to ethoxylate ALFOL-10 alcohol. In the alkoxylation reaction, 81 g of alcohol, 69 g of ethylene oxide and 0.5 g catalyst were employed. Reaction time was 102 minutes. The ethoxylated alcohol thus prepared contained 44.9% ethylene oxide and had the following distribution:

| Moles EO |  |
|---|---|
| 0 | 8.70 |
| 1 | 8.15 |
| 2 | 10.38 |
| 3 | 19.45 |
| 4 | 22.44 |
| 5 | 16.87 |
| 6 | 9.65 |
| 7 | 4.02 |
| 8 | 0.33 |
| 9 | 0.03 |

EXAMPLE 8

The procedure of Example 1 was followed in preparing catalysts with the exception that instead of using ALFONIC 1012-40 ethoxylated alcohol as the dispersant, various ethoxylated alcohols made in accordance with the teachings of U.S. Pat. No. 4,775,653 were used as dispersants, i.e., the dispersants were highly peaked alkoxylated alcohols. In general, the catalysts were prepared using the following formulation:

| 125 g | Dispersant |
|---|---|
| 11 g | $Ca(OH)_2$ |
| 2 g | $H_2SO_4$ |
| 11 g | Titanium IV isopropoxide |

Using the above general formulation, four different catalysts were prepared as follows:

| DISPERSANT | CATALYST |
|---|---|
| NOVEL II 1214-40[1] | A |
| NOVEL II 810-40[2] | B |
| NOVEL II 10-34[3] | C |
| NOVEL II 8-40[4] | D |

[1]$C_{12}$–$C_{14}$ alcohol ethoxylated with 40% by weight ethylene oxide and marketed by Vista Chemical Company.
[2]$C_8$–$C_{10}$ alcohol ethoxylated with 40% by weight ethylene oxide and marketed by Vista Chemical Company.
[3]$C_{10}$ alcohol ethoxylated with 34% by weight ethylene oxide (Experimental Material).
[4]$C_8$ alcohol ethoxylated with 40% by weight ethylene oxide (Experimental Material).

EXAMPLE 9

The catalysts prepared according to Example 8 were employed to ethoxylate ALFOL-10 alcohol as per the procedure of Example 1. Reaction parameters are shown in Table 6 below.

TABLE 6

|  | ALCOHOL g | CATALYST g | EO g | REACTION TIME min |
|---|---|---|---|---|
| CATALYST A | 81 | 1 | 69 | 315 |
| CATALYST B | 81 | 1 | 69 | 94 |
| CATALYST C | 81 | 1 | 69 | 74 |
| CATALYST D | 81 | 1 | 69 | 44 |

The ethylene oxide content and the distribution of ethylene oxide adducts of the ethoxylated alcohols prepared are shown in Table 7 below. For comparative purposes, similar data for an ethoxylated alcohol made in accordance with the process of U.S. Pat. No. 4,775,653 are also included.

TABLE 7

|  |  | '653 Catalyst | A | B | C | D |
|---|---|---|---|---|---|---|
| % EO |  | 46 | 44 | 45 | 46 | 44 |
| Moles EO | 0 | 7.0 | 11.1 | 7.4 | 6.6 | 7.5 |
|  | 1 | 6.5 | 9.2 | 8.5 | 7.4 | 8.8 |
|  | 2 | 11.0 | 10.3 | 12.7 | 13.3 | 14.4 |
|  | 3 | 19.4 | 18.3 | 22.2 | 26.2 | 23.1 |
|  | 4 | 23.4 | 20.2 | 23.3 | 22.7 | 22.4 |
|  | 5 | 17.8 | 16.1 | 15.7 | 16.2 | 14.2 |
|  | 6 | 9.6 | 9.0 | 7.1 | 8.0 | 6.3 |
|  | 7 | 3.7 | 3.8 | 2.4 | 3.0 | 2.1 |
|  | 8 | 1.1 | 1.4 |  |  |  |
|  | 9 |  |  |  |  |  |

EXAMPLE 10

This example demonstrates a variation in which the catalyst is prepared in situ, i.e. during the alkoxylation reaction. 0.93 g of the catalyst pre-mix of Example 1, prior to the addition of any titanium IV isopropoxide, was admixed with 81 g ALFOL 10 alcohol and 0.07 g titanium IV isopropoxide. The mixture was heated to drive-off water following which ethylene oxide was added to ethoxylate the ALFOL-10 alcohol as per the procedure of Example 2. During the reaction, 69 g of ethylene oxide was consumed over a reaction time of 67 minutes. The resulting ethoxylated alcohol contained 46% by weight ethylene oxide. The distribution of the ethylene oxide adducts of the ethoxylated alcohol produced are shown below:

| Moles EO |  |
|---|---|
| 0 | 6.0 |
| 1 | 7.3 |
| 2 | 11.7 |
| 3 | 21.7 |
| 4 | 23.8 |
| 5 | 16.8 |
| 6 | 8.1 |
| 7 | 3.0 |

As can be seen from the above data, the process of the present invention provides a catalyst and process for the ethoxylation of compounds containing active hydrogens e.g. alcohols, wherein the alkoxylated product has a narrowed or peaked distribution of the alkylene oxide adducts. Essentially, the degree of peaking that can be achieved is essentially the same as achieved using the catalyst and process of U.S. Pat. No. 4,775,653 when the catalyst is calcium based. As can best be seen with reference to Table 7, the use of highly peaked ethoxylated alcohols as dispersants tends to shift the adduct distribution toward lower mole ethylene oxide adducts as compared with materials made using the process of U.S. Pat. No. 4,775,653. The catalyst and process of the present invention is superior to that disclosed U.S. Pat. No. 4,775,653 in that the catalyst is, in general, easier to prepare and, as demonstrated by Example 10, the catalyst can be made "in situ" i.e. during the actual alkoxylation reaction. Also, the catalysts prepared according to the process of the present invention are less sensitive to air than catalysts using aluminum alkoxides such as disclosed in U.S. Pat. No. 4,775,653. It was also found that ethoxylated alcohols made using the process of the present invention have less volatiles than ethoxylated alcohols made using the catalyst and process of U.S. Pat. No. 4,775,653. This is significant in indicating an ethoxylated alcohol of lower odor, an especially desirable feature since the ethoxylated alcohols final widespread use in detergents commonly used in the home.

The foregoing disclosure and description of the invention is illustrative and explanatory thereof, and various changes in the method steps may be made within the scope of the appended claims without departing from the spread of the invention.

What is claimed is:

1. A process for the alkoxylation of an alcohol comprising:

forming a catalyst pre-mix by admixing an alkoxylated alcohol having the general formula $$R^1-O(C_mH_{2m}-O)_nH$$

where $R_1$ is a hydrocarbon radical containing from about 1 to about 30, carbon atoms, m is 2 to 4 and n is from about 1 to about 20, an alkaline earth metal containing compound selected from the group consisting of calcium compounds, strontium compounds and mixtures thereof and which is at least partially dispersible in said alkoxylated alcohol, an inorganic acid, and a titanium alkoxide having the general formula $$\begin{array}{c} OR_2 \\ | \\ RO_5-Ti-OR_3 \\ | \\ OR_4 \end{array}$$

where $R_2$, $R_3$, $R_4$ and $R_5$ is each a hydrocarbon radical containing from about 1 to about 30 carbon atoms, said alkaline earth containing compound and said alkoxylated alcohol being mixed prior to addition of said titanium alkoxide; and introducing an alcohol reactant and an alkylene oxide under alkoxylation conditions to thereby produce alkoxylated derivatives of said alcohol reactant.

2. The process of claim 1 including heating said catalyst pre-mix to a temperature and for a time sufficient to effect at least a partial exchange reaction between the alkoxide groups of said titanium alkoxide and said hydroxyl group of said alkoxylated alcohol and thereby form an active alkoxylation catalyst.

3. The process of claim 1 wherein $R_1$ is a hydrocarbon radical containing from about 6 to about 14 carbon atoms.

4. The process of claim 1 wherein n is from about 1 to about 12.

5. The process of claim 1 wherein n is from about 1 to about 4.

6. The process of claim 1 wherein $R_2$, $R_3$, $R_4$, and $R_5$ is each a hydrocarbon radical containing from about 2 to about 8 carbon atoms.

7. The process of claim 1 wherein said alkaline earth metal is calcium and said alkaline earth metal containing compound is selected from the group consisting of calcium oxide, calcium hydroxide and mixtures thereof.

8. The process of claim 1 wherein said inorganic acid is selected from the group consisting of sulfuric acid and hydrochloric acid.

9. The process of claim 1 wherein the mole ratio of said alkaline earth metal containing compound to said titanium alkoxide is from about 1:1 to about 10:1, calculated as alkaline earth metal and titanium, respectively.

10. The process of claim 1 wherein the mole ratio of said inorganic acid to said titanium alkoxide is from about 0.25:1 to about 4:1, calculated as acidic hydrogen and titanium, respectively.

11. The process of claim 2 including removing water from said pre-mix prior to the addition of said titanium alkoxide.

12. The process of claim 1 wherein said alkylene oxide comprises ethylene oxide.

13. The process of claim 1 wherein said alcohol is a monohydric aliphatic alcohol containing from 8 to 14 carbon atoms.

* * * * *